United States Patent [19]

Eliasson

[11] 4,159,325
[45] Jun. 26, 1979

[54] PHYSIOLOGICALLY ACTIVE COMPOSITION OF MATTER

[76] Inventor: Rune Eliasson, 13, Björnstigen, Vällingby, Sweden, 162 40

[21] Appl. No.: 839,950

[22] Filed: Oct. 6, 1977

[30] Foreign Application Priority Data

Oct. 7, 1976 [GB] United Kingdom ............... 41667/76

[51] Int. Cl.² .......................................... A61K 31/655
[52] U.S. Cl. ............................ 424/226; 424/DIG. 12
[58] Field of Search ........................ 424/226, DIG. 12

[56] References Cited

U.S. PATENT DOCUMENTS 4,045,429  10/1977  Agback ................................ 424/226

OTHER PUBLICATIONS

Physicians' Desk Reference, 30th Ed. (1976), pp. 1225–1227, 1324–1325 & 1339.

*Primary Examiner*—Donald B. Moyer
*Attorney, Agent, or Firm*—Lawrence Rosen; E. Janet Berry

[57] ABSTRACT

Temporary infertility in male human subjects is induced by oral administration of salicylazosulphonamides in doses ranging from 0.1 to 10 g per day.

3 Claims, No Drawings

PHYSIOLOGICALLY ACTIVE COMPOSITION OF MATTER

This invention relates to a physiologically active composition of matter and an object of the invention is to provide a composition of matter for human use having the property of inducing temporary male infertility.

BACKGROUND OF THE INVENTION

One way of inducing temporary male infertility is to suppress the production of spermatozoa in the testis. So far, all drugs tested in this respect for human use were aiming at this effect.

In animal experiments, however, another way has been tried, namely using drugs inducing a temporary infertility by altering the functional properties of the spermatozoa without interferring with their production.

Studies of such drugs are rather easily carried out when using animals as test objects, viz. by letting medicated males copulate with new females each time. The resulting number of litters will then be an objective measure of the effectivity of the drugs and can be used for evaluating the effect of the drug in question.

One of the most extensively studies drugs of this kind is α-chlorohydrin, which has proved very effective in rats, but less effective or totally ineffective in other animal species. These findings raise the problem of species specificity of reproductive processes as well as of the drugs influencing the said processes.

Obviously, testing male fertility in human studies is difficult and, even when possible, proves time consuming and disclosing that a number of factors may influence the functional properties of the spermatozoa.

Thus, studying of these problems during the last 15 years makes me believe that functional parameters, such as the mobility pattern and survival of the spermatozoa under different conditions, their metabolism, their uptake and release of specific substances, and their resistance to various physical and chemical factors, could be deciding for the ability of the spermatozoa to fertilize the ova.

THE INVENTION

The present invention is based upon the discovery that the spermatozoa of some men under treatment with salicylazosulphapyridine against ulcerative colitis showed an abnormal motility pattern and an abnormal uptake of zinc, and that the men were infertile while under such treatment. After ceasing the treatment there was a clear improvement in the functional properties of the men's spermatozoa. The same pattern in the functional properties of the spermatozoa was observed when administering the same drug to volunteers, and then stopping the treatment. In four cases, after ceasing the treatment, the wives became pregnant.

The invention accordingly relates to a composition of matter for use in controlling human male fertility, comprising as an active ingredient a compound of the formula:

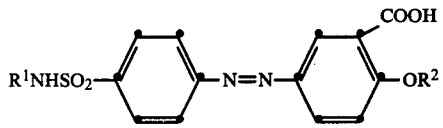

wherein $R^1$ represents a possibly substituted 5- to 6-membered heterocyclic group having one to two nitrogen atoms in the ring, and $R^2$ represents hydrogen or an acetyl group, or a salt or an ester of such compound, together with a pharmaceutically acceptable carrier, the said active ingredient making from 1% to 95% by weight of the composition.

Suitable salts are the alkalimetal salts, the ammonium salts, and physiologically inoccuous acid addition salts.

The preferred esters are lower-alkyl esters, such as the methyl, ethyl, propyl, isopropyl-, butyl, isobutyl and tert. butyl esters, and further esters of the grouping

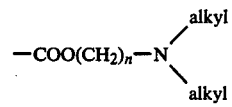

in which n is 2, 3 or 4, and the alkyl groups are straight chain groups having 1-4 carbon atoms.

Examples of the heterocyclic group represented by $R^1$ are the pyridine, pyrazine, pyrimidine, pyridazine, pyrrole, pyrazole, and imidazole groups, possibly carrying one or more lower-alkyl groups, such as methyl, ethyl, propyl, and butyl groups.

A preferred active ingredient of the present compositions is salazopyrin (salicylazo-sulphapyridine), and alkalimetal or ammonium salt thereof or an acid addition salt thereof with a pharmacologically innocuous acid.

Another preferred active ingredient is salazosulphadimidine (salicylazosulpha-3,5-dimethylpyrimidine) or a salt thereof as specified above.

The said compounds are very low toxicity and apparently with negligible side effects. By administering in doses ranging from 0.5 to 10 g per day, the preferred doese being 1.5-3 per day, the men became infertile, and this state could be maintained even by reduced daily doses.

The effect of the active ingredient can be ascertained by periodically testing the semen of the medicated persons for changes in the motility of the spermatozoa and in the uptake of zinc, such testing showing also that the effect gradually disappears during the next two days if the medication is not repeated.

Accordingly, this invention provides a method for controlling fertility in a human male subject, the method comprising administering a composition of the type described above to the subject.

The compositions of the invention are preferably made up for oral application in the shape of tablets, dragées, capsules, pills, solutions or suspensions, each unit or dose containing at least 100 mg, and preferably 500 mg of the active component.

The following Example is illustrative of the components of a dosage unit in the form of a tablet.

| Example | | |
|---|---|---|
| Salazopyrin | 500 | mg |
| Polyvinylpyrrolidone | 17 | mg |
| Colloidal silica | 2.5 | mg |
| Magnesium stearate | 6 | mg |

I claim:

1. A method of inducing temporary infertility in human males which comprises orally administering salicyalzosulphapyridine or pharmacologically acceptable salts or esters thereof in an amount sufficient to produce temporary infertility.

2. The method of claim 1 wherein salicylazo-sulphapyridine is orally administered to said human males.

3. The method of claim 1 wherein the salicylazo-sulphapyridine is orally administered to said human males in does ranging from 0.5 to 10 grams per day.

* * * * *